United States Patent
Mawdsley et al.

(10) Patent No.: US 10,968,465 B2
(45) Date of Patent: Apr. 6, 2021

(54) BIOLOGICAL CONVERSION AND PRODUCT RECOVERY PROCESSES

(71) Applicant: LanzaTech, Inc., Skokie, IL (US)

(72) Inventors: Michael James Harry Mawdsley, Skokie, IL (US); Michael Emerson Martin, Skokie, IL (US); Kathleen Frances Smart, Skokie, IL (US); Rachel Jane Brenc, Skokie, IL (US)

(73) Assignee: LANZATECH, INC., Skokie, IL (US)

( * ) Notice: Subject to any disclaimer, the term of this patent is extended or adjusted under 35 U.S.C. 154(b) by 196 days.

(21) Appl. No.: 16/007,505

(22) Filed: Jun. 13, 2018

(65) Prior Publication Data

US 2018/0355383 A1    Dec. 13, 2018

Related U.S. Application Data

(60) Provisional application No. 62/518,895, filed on Jun. 13, 2017.

(51) Int. Cl.
| | | |
|---|---|---|
| *C12P 7/16* | (2006.01) | |
| *C12P 7/06* | (2006.01) | |
| *C12N 9/02* | (2006.01) | |
| *C12N 9/10* | (2006.01) | |
| *C12P 7/04* | (2006.01) | |

(52) U.S. Cl.
CPC ............ *C12P 7/065* (2013.01); *C12N 9/0004* (2013.01); *C12N 9/1025* (2013.01); *C12P 7/04* (2013.01); *C12P 7/16* (2013.01); *C12Y 101/01001* (2013.01); *C12Y 101/01002* (2013.01); *C12Y 102/07005* (2013.01); *C12Y 203/01008* (2013.01); *C12Y 207/02001* (2013.01)

(58) Field of Classification Search
CPC combination set(s) only.
See application file for complete search history.

(56) References Cited

U.S. PATENT DOCUMENTS

| | | |
|---|---|---|
| 8,026,290 B2 | 11/2011 | Hensley |
| 8,574,879 B2 | 11/2013 | Gaddy et al. |
| 2003/0211585 A1 | 11/2003 | Gaddy |
| 2007/0144886 A1 | 6/2007 | Sylvester et al. |

FOREIGN PATENT DOCUMENTS

| | | |
|---|---|---|
| WO | 2007117157 | 10/2007 |
| WO | 2008115080 | 9/2008 |
| WO | 2009022925 | 2/2009 |
| WO | 2010093262 | 8/2010 |
| WO | 2011002318 | 1/2011 |

OTHER PUBLICATIONS

Abubackar et al., "Carbon monoxide fermentation to ethanol by Clostridium autoethanogenum in a bioreactor with no accumulation of acetic acid," Bioresource Technology 186:122-127 (2015).
Diender et al., "Production of medium-chain fatty acids and higher alcohols by a synthetic co-culture grown on carbon monoxide or syngas," Biotechnology for Biofuels 9:1-11 (2016).
Liew et al., "Metabolic engineering of Clostridium autoethanogenum for selective alcohol production," Metabolic Engineering 40:104-114 (2017).
Written Opinion of the International Searching Authority for International Application No. PCT/US2018/037283, dated Jan. 21, 2019 (pp. 1-5).
Gomez-Manzo et al., Int J. Mol Sci, Jan. 2015, 1293-311, 16(1).
Bridhar et al., Appl Environ Microbiol., Jan. 2000, 246-51, 66 (1).

*Primary Examiner* — Heidi Reese
(74) *Attorney, Agent, or Firm* — Stephen M. Chong

(57) ABSTRACT

The invention provides a process for reducing bio-catalytic oxidation of a product in a post-production stream. More particularly the invention provides a process for reducing bio-catalytic oxidation of an alcohol in a product stream, the product stream comprising an alcohol product, dissolved carbon dioxide, and at least one enzyme capable of oxidizing the alcohol. The invention finds applicability in fermentation processes, wherein a C1-fixing microorganism utilizes a C1-containing substrate to produce a fermentation product.

19 Claims, 6 Drawing Sheets

BIOLOGICAL CONVERSION AND PRODUCT RECOVERY PROCESSES

BACKGROUND OF THE INVENTION

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). The majority of $CO_2$ comes from the burning of fossil fuels to produce energy, although industrial and forestry practices also emit $CO_2$ into the atmosphere. Reduction of greenhouse gas emissions, particularly $CO_2$, is critical to halt the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of carbon in such gases. In particular, C1-fixing microorganisms have been demonstrated to convert gases containing $CO_2$, CO, and/or $H_2$ into products such as ethanol and 2,3-butanediol.

Environmental concerns over fossil fuel greenhouse gas (GHG) emissions have led to an increasing emphasis on renewable energy sources. As a result, ethanol is rapidly becoming a major hydrogen-rich liquid transport fuel around the world. Continued growth in the global market for the fuel ethanol industry is expected for the foreseeable future, based on increased emphasis on ethanol production in Europe, Japan, and the United States, as well as several developing nations. For example, in the United States, ethanol is used to produce E10, a 10% mixture of ethanol in gasoline. In E10 blends, the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. In addition, the European Union (EU) has mandated targets, for each of its member nations, for the consumption of sustainable transport fuels such as biomass-derived ethanol.

The vast majority of fuel ethanol is produced via traditional yeast-based fermentation processes that use crop-derived carbohydrates, such as sucrose extracted from sugarcane or starch extracted from grain crops, as the main carbon source. However, the cost of these carbohydrate feed stocks is influenced by their value in the marketplace for competing uses, namely as food sources for both humans and animals. In addition, the cultivation of starch or sucrose-producing crops for ethanol production is not economically sustainable in all geographies, as this is a function of both local land values and climate. For these reasons, it is of particular interest to develop technologies to convert lower cost and/or more abundant carbon resources into fuel ethanol. In this regard, carbon monoxide (CO) is a major, energy-rich by-product of the incomplete combustion of organic materials such as coal, oil, and oil-derived products. CO-rich waste gases result from a variety of industrial processes. For example, the steel industry in Australia is reported to produce and release into the atmosphere over 500,000 metric tons of CO annually.

More recently, microorganism (bacterial) based process alternatives for producing ethanol from CO on an industrial scale have become a subject of commercial interest and investment. The ability of microorganism cultures to grow, with CO being the sole carbon source, was first discovered in 1903. This characteristic was later determined to reside in an organism's use of the acetyl coenzyme A (acetyl CoA) biochemical pathway of autotrophic growth (also known as the Woods-Ljungdahl pathway and the carbon monoxide dehydrogenase/acetyl CoA synthase (CODH/ACS) pathway). A large number of anaerobic organisms including carboxydotrophic, photosynthetic, methanogenic, and acetogenic organisms have since been shown to metabolize CO. Anaerobic bacteria, such as those from the genus *Clostridium*, are known to produce ethanol from CO, $CO_2$ and $H_2$ via the acetyl CoA biochemical pathway. For example, various strains of *Clostridium ljungdahlii* that produce ethanol from gases are described in WO 00/68407; EP 1117309 A1; U.S. Pat. Nos. 5,173,429; 5,593,886; 6,368,819; WO 98/00558; and WO 02/08438. The bacterium *Clostridium autoethanogenum* sp is also known to produce ethanol from gases (Abrini et al., Archives of Microbiology 161: 345-351 (1994)).

Because of an organism's enzyme specificity, selectivity to a certain product can be very high (100%), enabling microbial synthesis routes to achieve higher yields than Fisher Tropsch (FT) catalysis. Other benefits over FT catalysis include operation at near ambient temp and near atmospheric pressure; and an ability to use varying ratios of CO, $H_2$, and $CO_2$. In addition, concerns over the poisoning of catalysts, due to impurities in the reaction medium, are diminished. Despite these apparent advantages associated with the microbial synthesis of ethanol from CO, such processes must nonetheless be competitive with other technologies, in terms of ensuring that the production rate is competitive. When using CO as their carbon and energy source, the anaerobic bacteria described above produce ethanol by fermentation, but they also produce at least one other metabolite, for example $CO_2$, methane, n-butanol, and/or acetic acid. The formation of any of these metabolites has the potential to significantly impact productivity and overall economic viability of a given process, as available carbon is lost to the metabolite(s) and the production efficiency of the desired end product is compromised. In addition, unless a metabolite (e.g., acetic acid) itself has value at the time and place of the microbial fermentation process, it may pose a waste disposal problem. Various proposals for addressing the formation of products other than the desired end product in the anaerobic fermentation of CO-containing gases to make ethanol are discussed in WO2007/117157, WO2008/115080 and WO2009/022925.

Ethanol production rate, which is a key determinant as to whether a given fermentation process is economically attractive, is highly dependent on managing the appropriate conditions for bacterial growth. For example, it is known from WO2010/093262 that the CO-containing substrate must be provided to a microbial culture at a rate that results in optimal microbial growth and/or desired metabolite production. If insufficient substrate is provided, microbial growth slows and the fermentation product yields shift toward acetic acid at the expense of ethanol. If excessive substrate is provided, poor microbial growth and/or cell death can result. Further information regarding the relationships among operating parameters in these processes is found in WO2011/002318.

The art of biological processes for producing ethanol from CO, and particularly CO-containing waste streams such as the gaseous effluents emitted in industrial processes, is continually seeking solutions that improve process economics and therefore industry competitiveness. One area of interest relates to preserving the yield of a desired product in a fermentation broth downstream of the bioreactor, before the product recovery stage. Many C1-fixing microorganisms capable of producing ethanol are also able to oxidise ethanol to other products under certain conditions. Conditions which enable the oxidation of ethanol may be found at ethanol production facilities. The microbial oxidation of ethanol, prior to the ethanol product being recovered, represents a loss of the desired ethanol product.

SUMMARY OF THE INVENTION

Aspects of the invention relate to improvements in biological conversion and product recovery processes.

In one aspect the invention provides a process for reducing bio-catalytic oxidation of ethanol in a product stream. In one embodiment, the product stream comprises an alcohol, dissolved carbon dioxide ($CO_2$) and at least one enzyme capable of oxidising the alcohol. In certain embodiments the product stream is flowed from a bioreactor to a pre-product recovery zone, and treated to reduce the conversion of the alcohol to its corresponding carboxylic acid.

In one embodiment, the product stream comprises (i) ethanol, (ii) dissolved carbon dioxide, and (iii) a microbial culture comprising at least one microorganism capable of oxidising ethanol. In one embodiment the microorganism is a C1-fixing microorganism having one or more enzymes capable of converting ethanol to acetate.

In one embodiment, treating the product stream (i.e. the treatment step) comprises sparging the product stream with an inert gas. The inert gas sparged into the product stream displaces at least a portion of dissolved $CO_2$ from the product stream. In certain embodiments, the inert gas displaces substantially all the dissolved $CO_2$ from the product stream. Examples of suitable inert gases include, but are not limited to nitrogen and methane. In preferred embodiments, the inert gas is nitrogen. In alternative embodiments, hydrogen is used to displace the dissolved $CO_2$ from the product stream.

In one embodiment, the treatment step comprises increasing the temperature of the product stream. In certain embodiments, the temperature of the product stream is increased to a temperature at which the enzyme capable of oxidising ethanol is inactivated. In one embodiment, the temperature of the product stream is increased to at least 50° C., or at least 60° C., or at least 70° C., or at least 75° C., or at least 78° C. In one embodiment, the temperature of the product stream is maintained at above the determined temperature for at least 10 seconds, or at least 20 seconds, or at least 30 seconds, or at least 1 minute, or at least 2 minutes, or at least 3 minutes, or at least 5 minutes, or at least 10 minutes. Preferably, the temperature of the product stream is maintained at above the determined temperature for between 10 seconds to 30 seconds, or between 10 seconds to one minute, or between 10 seconds to two minutes. In one embodiment, the temperature of the product stream is increased to at least 60° C., and maintained at this temperature for at least 1 minute. In one embodiment, the temperature of the product stream is increased to at least 75° C., and maintained at this temperature for at least 5 minutes.

In one embodiment, the treatment step comprises depressurization of the product stream. In one or more embodiment, the bioreactor is operated at pressure, thereby resulting in a pressurized product stream. In one or more embodiment, when the bioreactor is operated at pressure, the product stream is treated by being depressurized. In one or more embodiment, depressurization of the product stream occurs in a separate vessel. In one embodiment, the depressurization occurs at atmospheric pressure in a holding tank. In certain embodiments, depressurization provides for flashing of dissolved $CO_2$ from the product stream, which results in the displacement of the dissolved $CO_2$ from the product stream. In one embodiment, the pressure of the product stream is at least 0.25 barg, or at least 0.5 barg, or at least 1.0 barg, or at least 1.5 barg, or at least 2.0 barg, or at least 2.5 barg, or at least 3.0 barg before being depressurized. In one embodiment, the pressure of the product stream is maintained above atmospheric pressure for at least 1 second, or at least 10 seconds, or at least 15 seconds, or at least 20 seconds, or at least 25 seconds, or at least 30 seconds before being depressurized. Preferably, the pressure of the product stream is maintained at above atmospheric pressure for between 1 to 30 seconds, or between 1 second to 15 seconds, or between 15 seconds to 30 seconds before being depressurized. In one embodiment, the pressure of the product stream is at least 2.0 barg, and maintained at this pressure for at least 1 second before being depressurized. In one embodiment, the pressure of the product stream is at least 0.25 barg, and maintained at this pressure for at least 30 seconds before being depressurized.

In one embodiment, the biomass comprises at least one C1-fixing microorganism. In one embodiment, the C1-fixing microorganism comprises at least one enzyme selected from the group consisting of alcohol dehydrogenase, aldehyde dehydrogenase, acetate kinase, and phosphotransacetylase.

In one embodiment, the biomass comprises at least one non-C1-fixing microorganism. In one embodiment, the non-C1-fixing microorganism comprises at least one enzyme selected from the group consisting of alcohol dehydrogenase, aldehyde dehydrogenase, acetate kinase, and phosphotransacetylase. In one or more embodiment, the non-C1-fixing microorganism is *Acetobacter*.

In one embodiment the invention comprises feeding a C1-containing substrate to a bioreactor system comprising at least a first bioreactor including a culture medium and a C1-fixing bacterium to metabolize a carbon source in the C1-containing substrate and produce at least one fermentation product; withdrawing from the bioreactor system a bleed stream comprising bacterium, sparging the bleed stream with nitrogen to displace a $CO_2$ component in the bleed stream, and passing the $CO_2$ depleted stream to a product recovery zone to recover at least one fermentation product.

In an alternative embodiment the invention comprises feeding a C1-containing substrate to a bioreactor system comprising at least a first bioreactor including a culture medium and a bacterium to metabolize a carbon source in the substrate and produce at least one fermentation product; withdrawing from the bioreactor system a bleed stream comprising bacterium, heating the bleed stream to denature one or more enzymes contained in the bleed stream and provide a treated stream, and passing the treated stream to a product recovery zone to recover at least one fermentation product.

In an alternative embodiment, the invention comprises feeding a C1-containing substrate to a pressurized bioreactor comprising at least a first bioreactor including a culture medium and a bacterium to metabolize a carbon source in the substrate and produce at least one fermentation product; withdrawing from the pressurized bioreactor system a bleed stream comprising bacterium, depressurizing the bleed stream to displace a $CO_2$ component in the bleed stream through flashing, and passing the $CO_2$ depleted stream to a product recovery zone to recover at least one fermentation product.

In one embodiment, the C1-fixing bacterium is selected from the group consisting of *Clostridium, Moorella* and *Acetobacterium*. In one embodiment, the C1-fixing bacterium is selected from the group consisting of *Clostridium autoethanogenum, Clostridium ljungdahlii*, and *Clostridium ragsdalei*.

In one embodiment, the pre-product recovery zone encompasses one or more vessels and/or conduits, provided downstream of a production zone and upstream of a product recovery zone. In one embodiment, the production zone is a bioreactor, and the product recovery zone is a distillation zone. In one embodiment the pre-product recovery zone is a storage vessel. In one embodiment the storage vessel is a holding tank. The pre-product recovery zone further comprises one or more liquid conduits provided to feed the bleed stream from the bioreactor to the holding tank, and from the holding tank to the product recovery module. In one embodiment, bleed is fed from the bioreactor through conduits directly to the product recovery zone. In certain embodiments, a first portion of the bleed is provided directly to the product recovery zone, and a second portion of the bleed is provided to a holding tank.

In a second aspect, the invention provides a process for reducing bio-catalytic oxidation of ethanol in a product stream, wherein the product stream comprises ethanol, $CO_2$, and at least one enzyme capable of oxidising ethanol, the process comprising (i) flowing the product stream from a bioreactor to a pre-product recovery zone; and (ii) treating the product stream to reduce the conversion of ethanol to acetate. In one embodiment, the product stream is produced in a cell-free system.

DETAILED DESCRIPTION OF THE INVENTION

Figure 1:
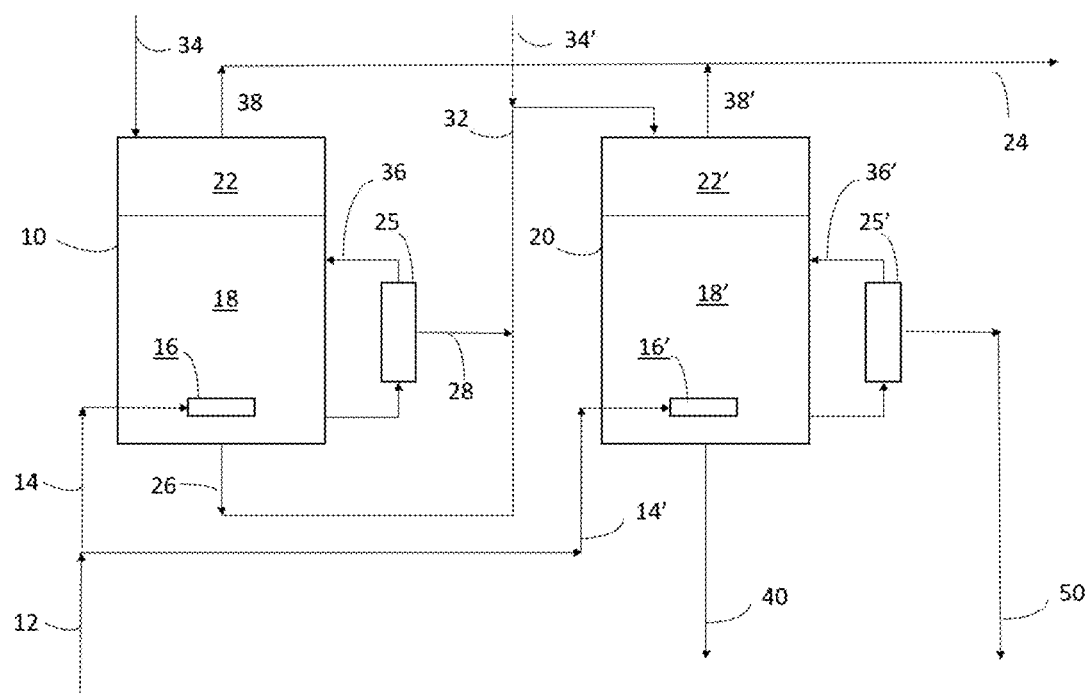
FIG. 1 depicts a representative bioreactor system utilizing two bioreactors.

In commercial scale production operations, it is common for a product stream to be sent to a storage means prior to being sent to a product recovery zone. The inventors have found that when there is a delay in processing of a product stream, undesirable reactions, which may result in conversion of a desired end product to an undesired product may occur. By preventing such reactions, the yield of the desired product can be preserved.

The inventors have developed processes to substantially reduce, or prevent undesirable reactions in a post-production stream which may result in conversion of a desired end product to an undesired product. The present invention can be applied to fermentation technologies, particularly gas fermentation processes that use acetogenic bacteria. Additionally, the invention can be applied to cell-free technology processes, to prevent back reactions of one or more enzymes in a cell-free production process.

Whilst the description that follows pertains to ethanol fermentations, it is considered that the teachings are equally applicable to other primary alcohol fermentation processes and purification processes. Furthermore, whilst the embodiments provided relate to gas fermentation processes, it is considered that the invention would be applicable to any fermentation process generating a fermentation broth containing fermentation product(s) and one or more enzymes capable of oxidising the fermentation product(s). In one embodiment, the fermentation product is a primary alcohol, and the one or more enzymes is an enzyme capable of converting the primary alcohol to its corresponding carboxylic acid. Exemplary primary alcohols include, but are not limited to butanol, 1-propanol and 1-octanol. Furthermore, whilst the invention is applicable to fermentation products produced by a production strain, the invention also applies to products excreted by any contaminant microorganism that may be present in the bioreactor.

The term "permeate stream" is a liquid stream withdrawn from a bioreactor that has been treated to remove a biomass component. Typically, biomass is removed via filtration, and returned to the bioreactor.

The term "bleed stream" refers to a liquid stream withdrawn from a bioreactor. Typically, the bleed stream is unfiltered, and comprises biomass, liquid products and dissolved and entrained gases.

The term "product stream" refers to a liquid stream comprising at least one product, for example ethanol. Preferably the product stream is a stream that has exited a production process. For example, a product stream may be a liquid stream exiting a bioreactor, prior to being received by a product recovery means. The product stream may be a permeate stream or a bleed stream. The product stream may be a combined bleed stream and permeate stream.

The term "bio-catalytic oxidation" refers to the process whereby a primary alcohol (i.e. ethanol) is oxidised to its corresponding acid (i.e. acetate), due to the presence of one or more enzymes capable of this reaction. The one or more enzymes may be provided in a cell-free system, or may be contained in a bacterial culture.

The term "pre-product recovery zone" refers to a zone downstream of the bioreactor and upstream of product recovery module. The pre-product recovery zone receives at least one of a bleed stream and/or a permeates stream which exits the bioreactor via at least one outlet, and feeds said product stream to a product recovery means, such as a distillation means. The pre-product recovery comprises at least one conduit for passing a product stream from a bioreactor system to a product recovery module, and may further contain a storage vessel such as a holding tank, which functions to store a portion of a product stream before passing the product stream to the product recovery module.

The term "dissolved $CO_2$" refers to $CO_2$ present in a liquid stream in the form of a dissolved gas. Dissolved $CO_2$ may be provided in a number of liquid streams, including but not limited to a fermentation broth, a liquid nutrient media, a bleed stream, a permeate stream or a product stream.

The term "entrained $CO_2$" refers to entrapment of $CO_2$ gas bubbles in a liquid stream. Entrained $CO_2$ may be provided in a number of liquid streams, including but not limited to a fermentation broth, a liquid nutrient media, a bleed stream, a permeate stream or a product stream.

Typically, the fermentation is performed in a bioreactor. The term "bioreactor" includes a culture/fermentation device consisting of one or more vessels, towers, or piping arrangements, such as a continuous stirred tank reactor (CSTR), immobilized cell reactor (ICR), trickle bed reactor (TBR), bubble column, gas lift fermenter, static mixer, or other vessel or other device suitable for gas-liquid contact. In some embodiments, the bioreactor may comprise a first growth reactor and a second culture/fermentation reactor. The substrate may be provided to one or both of these reactors. As used herein, the terms "culture" and "fermentation" are used interchangeably. These terms encompass both the growth phase and product biosynthesis phase of the culture/fermentation process.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas-liquid transfer. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure.

In certain embodiments, the fermentation is performed in the absence of light or in the presence of an amount of light insufficient to meet the energetic requirements of photosynthetic microorganisms. In certain embodiments, the microorganism of the invention is a non-photosynthetic microorganism.

During normal operation of a bioreactor system, the net generation of liquid products requires that these products be withdrawn, preferably on a continuous basis, to prevent their accumulation in each bioreactor and thereby maintain steady-state conditions. If all of the withdrawn liquid has the same, bulk composition as that existing in the bioreactor (including the same concentrations of bacteria and culture medium components), then the bioreactor, although operating at steady-state with respect to ethanol and acetic acid concentration, would become steadily depleted in bacteria concentration. Under such circumstances, a greater productivity of ethanol relative to the productivity (growth) of bacteria would result directionally in a faster rate of bacteria depletion from a given bioreactor. In order to maintain bacteria concentration by providing an additional operating degree of freedom, liquid products may be withdrawn from a given bioreactor, as either an unfiltered stream (i.e. a bleed stream) or a filtered stream (i.e. a permeate stream). The bleed stream, is an unfiltered stream having substantially the same bulk composition as the fermentation broth existing in the bioreactor, or at least substantially the same bacteria concentration. The filtered stream is a stream withdrawn from the bioreactor and passed to a filtration means, where the stream is filtered to provide a retentate that is enriched in bacteria and returned to bioreactor to maintain its bacteria concentration, and a permeate. The permeate stream, which is substantially free of biomass, is not recycled to the bioreactor. This permeate may then be passed to a downstream bioreactor, or may be passed to a product recovery zone.

The withdrawal of both bleed and permeate streams provides for a significantly improved degree of overall process control, especially in terms of managing the bacteria concentration in a bioreactor at varying levels of productivity. As the rate of ethanol generation increases, the flow of the permeate stream relative to the flow of the bleed stream can be increased, allowing more filtered reactor liquid to be withdrawn with greater retention of bacteria. Because ethanol is present in both of these withdrawn streams, the bleed and permeate streams that are ultimately withdrawn from a bioreactor system, for example from a final stage bioreactor (such as from a second bioreactor of a bioreactor system comprising first and second bioreactors operating in series with respect to liquid flow), are normally both further processed for ethanol purification. The bleed and permeate streams are sent to storage zones, with effluents from these tanks then sent to downstream recovery units.

Target products may be separated or purified from the effluents from the storage tanks using any method or combination of methods known in the art, including, for example, fractional distillation, evaporation, pervaporation, gas stripping, phase separation, and extractive fermentation, including for example, liquid-liquid extraction. In certain embodiments, target products are recovered from the fermentation broth by continuously removing a portion of the broth from the bioreactor, separating microbial cells from the broth (conveniently by filtration), and recovering one or more target products from the broth. Alcohols and/or acetone may be recovered, for example, by distillation. Acids may be recovered, for example, by adsorption on activated charcoal. Separated microbial cells are preferably returned to the bioreactor. The cell-free permeate remaining after target products have been removed is also preferably returned to the bioreactor. Additional nutrients (such as B vitamins) may be added to the cell-free permeate to replenish the medium before it is returned to the bioreactor.

In typical production facilities, conditions which enable the oxidation of ethanol may be found downstream of the bioreactor and upstream of the product recovery means (i.e. in a storage zone). Particularly it has been found, that an ethanol target product can be impacted by the presence of viable bacteria in the bleed stream. When $CO_2$ is present in the bleed stream along with viable bacteria capable of oxidising ethanol, the ethanol product can be oxidised by the bacteria to produce acetate. As bleed and permeate streams are continuously removed from the bioreactors and sent to a storage zone prior to product recovery, this represents either the loss of targeted products (i.e. ethanol), and/or production of non-targeted products (i.e. acetate) that may require separation and or treatment. The inventors have identified processes for reducing, conversion of ethanol to acetate, thereby preserving the ethanol yield.

Ethanol Oxidation Reaction

Typically, in C1-fixing microorganism that use the Wood-Ljungdahl pathway, utilization and generation of ethanol proceeds via acetyl-CoA, acetate and acetaldehyde using $NAD(P)^+$-dependent acetaldehyde and ethanol dehydrogenases and reduced ferredoxin dependent aldehyde:ferredoxin oxidoreductase (AOR) (Kopke et al). Ethanol production is driven by surplus of reducing equivalents, which are generated from CO and $H_2$ oxidation. The microorganism balances the surplus of reducing equivalents by forming reduced products (i.e. ethanol). Reducing equivalents include reduced ferredoxin ($Fd_{red}$), NADPH, and NADH.

Reducing equivalents are predominantly formed in CO oxidation reaction by carbon monoxide dehydrogenase (CODH) ($Fd_{red}$) or Hydrogenase (($Fd_{red}$), NADH, NAD(P)H or mixtures thereof). The reducing equivalents formed by the CO oxidation reaction can be consumed by ethanol formation. There are two routes to ethanol production. The first route is via a NADPH or NADH dependent reaction, wherein, acetyl—CoA is reduced to ethanol via acetaldehyde as shown by the following stoichiometry:

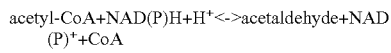
acetyl-CoA+NAD(P)H+H$^+$<->acetaldehyde+NAD(P)$^+$+CoA

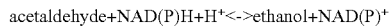
acetaldehyde+NAD(P)H+H$^+$<->ethanol+NAD(P)$^+$

The second route is via acetate. The production of acetate from acetyl-CoA involves the transfer of phosphate coupled with an ATP generation step as shown by the following stoichiometry:

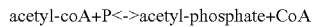
acetyl-coA+P<->acetyl-phosphate+CoA

acetyl-phosphate+ADP<->acetate+ATP

Acetate is then reduced to acetaldehyde and further reduced to ethanol. The formation of acetaldehyde is driven by reduced ferredoxin, and the formation of ethanol from acetaldehyde is NAD(P)H dependent, as shown by the following stoichiometry:

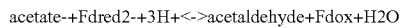
acetate-+Fdred2-+3H+<->acetaldehyde+Fdox+H2O

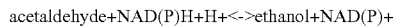
acetaldehyde+NAD(P)H+H+<->ethanol+NAD(P)+

In situations, where there is not a surplus of reducing equivalents (i.e. there is a lack of CO oxidation because there is less substrate available), there is less driving force to produce ethanol, and the microorganism can consume ethanol as a substrate, oxidizing it to form additional acetyl-CoA and acetate, thereby replenishing NAD, NADP, and $Fd_{ox}$. In a post fermentation liquid stream, such as a bleed stream, when the fermentation substrate is limited or no longer available, the microorganism can utilize ethanol and produce acetate.

Each of the reactions referenced work in both directions. A number of factors determine the direction in which the reactions proceed, including, but not limited to kinetics, substrate availability, co-factor levels, and pH.

$CO_2$ is cofactor of both carbon monoxide dehydrogenase (CODH), an enzyme responsible for the following reaction: $CO+H_2O+Fd_{ox}$<->$CO_2+Fd_{red}$, and pyruvate:ferredoxin-oxidoreductase (PFOR), and enzyme responsible for the following reaction: Acetyl-CoA+$CO_2$+$Fd_{red}$<->Pyruvate+CoA+$Fd_{ox}$. Increased levels of $CO_2$ will shift the reaction balance of CODH away from CO oxidation, the reaction balance of PFOR towards pyruvate formation. Both these shifts result in a lower level of reducing equivalents $Fd_{red}$, providing conditions that make ethanol oxidation favourable. This can be counteracted by reducing the amount of $CO_2$, or removing $CO_2$ from the bleed stream.

Without wishing to be bound by theory, the inventors consider that the ethanol oxidation reaction occurs during the fermentation process, however under fermentation conditions the reaction to produce ethanol occurs at a much greater rate than the oxidation of ethanol, and the reaction has little effect on product titres. When the fermentation broth is removed from the bioreactor, and ethanol product is no longer being produced by the microorganisms, the ethanol oxidation reaction becomes problematic.

The inventors have developed processes to substantially reduce, or prevent these undesirable reactions in the bleed stream after the fermentation stage of the process, thereby preserving the concentration of the desired end product in the bleed stream from the time at which the bleed stream exits the fermentation process to when it is introduced to a product recovery processes.

In one embodiment, the process is directed to removing dissolved, entrained or suspended $CO_2$ from the bleed stream. This is achieved by sparging the bleed stream with nitrogen gas, which displaces $CO_2$ from solution. As $CO_2$ is essential to the reaction for conversion of ethanol to acetate, removal of $CO_2$ from the bleed stream prevents oxidation of ethanol from occurring via this mechanism.

In order for this process to be effective, an inert gas, such as nitrogen must be sparged such that the majority of $CO_2$ provided in the bleed stream is displaced. Preferably substantially all of the $CO_2$ in the bleed stream is displaced. Ideally, the majority of $CO_2$ in the bleed stream should be displaced in less than 5 minutes, or less than 10 minutes, or less than 15 minutes, or less than 20 minutes, or less than 30 minutes.

Nitrogen may be sparged into the bleed stream to displace $CO_2$ either in the holding tank, or in a conduit for feeding the bleed stream from the bioreactor to the holding tank. In one embodiment nitrogen is continuously fed into a headspace in the holding tank, whilst gas is constantly purged from the headspace. Providing nitrogen to the headspace of the holding tank enables displacement of $CO_2$ from liquid in contact with the headspace gas. The holding tank can be blanketed with nitrogen, a process whereby smaller amounts of nitrogen are fed to the reactor, resulting in some $CO_2$ displacement. Alternatively, a nitrogen sweep can be performed on the holding tank, wherein greater amounts of nitrogen are fed to the holding tank, resulting in greater levels of $CO_2$ displacement. In an alternative embodiment, nitrogen is sparged into the bleed stream via a conduit provided in a lower portion of the holding tank. Sparging of the nitrogen gas at or towards the bottom of the holding tank encourages active displacement of $CO_2$ from the bleed stream.

In one embodiment, nitrogen is fed into the headspace of the holding tank, and the bleed stream is sprayed through the headspace of the holding tank via one or more nozzles. By spraying the bleed stream into the nitrogen rich headspace, a greater portion of the $CO_2$ in the bleed stream is displaced as the surface area of bleed stream is increased. The size of the nozzle can be adjusted to alter the droplet size of the spray. Preferably the energy required to spray the bleed stream into the headspace is provided by the bioreactor. Liquid exiting the bioreactor is typically at least at 3 barg or higher, which is sufficient to reach the holding vessel and overcome pressure drop across standard spray nozzles.

In one embodiment, nitrogen is sparged into the bleed stream via an in-line sparger provided in a conduit for feeding the bleed stream from the bioreactor to the holding tank. Preferably, the inline conduit is provided proximal to the holding tank.

It is preferable for nitrogen (or other inert gas) to be sparged into the bleed stream when the bleed stream is at, or close to ambient pressure. $CO_2$ is more soluble at higher pressures, so displacing the $CO_2$ component will be less efficient when nitrogen is sparged into a bleed stream at higher pressures.

Preferably, the inert gas provided to the bleed stream is nitrogen. Alternatively, the inert gas is hydrogen or methane. In one embodiment, the bleed stream is sparged with air. In one embodiment the air-sparged bleed stream undergoes one or more additional treatment stages prior to being passed to the product recovery module.

In one embodiment, there is provided a process for heating the bleed stream. In one embodiment, the method comprises applying heat to the bleed stream, containing live cells, such that at least one of the following occurs: (i) proteins required for the oxidation of ethanol are denatured, (ii) the bacterial cells are lysed, and (iii) cell metabolism is disrupted.

Preferably the bleed stream is heated to a temperature sufficient to denature one or more enzymes capable of converting ethanol to acetate. In one embodiment the one or more enzymes are selected from the group consisting of NADH dependent alcohol dehydrogenase (EC1.1.1.1), NADPH dependent alcohol dehydrogenase (EC1.1.1.2), aldehyde: ferredoxin oxiodreductase (AOR, EC1.2.7.5), acetate kinase (EC2.1.2.1), and phosphotransacetylase (EC 2.3.1.8).

Ideally, the bleed cell is heated to a desired temperature within a short period of time, after exiting the bioreactor. For example, the bleed stream is heated to the desired temperature within 30 minutes of exiting the bioreactor, or within 20 minutes of exiting the bioreactor, or within 10 minutes of exiting the bioreactor, or within 5 minutes of exiting the bioreactor, or within 1 minute of exiting the bioreactor.

The desired temperature of the product stream is increased to at least 50° C., or at least 60° C., or at least 70° C., or at least 75° C., or at least 78° C. In one embodiment, the temperature of the product stream is maintained at above the determined temperature for at least 10 seconds, or at least 20 seconds, or at least 30 seconds, or at least 1 minute, or at least 2 minutes, or at least 3 minutes, or at least 5 minutes, or at least 10 minutes.

The bleed stream can be heated by conventional means known in the art, including but not limited to plate and frame heat exchangers, and shell and tube heat exchangers. It is preferable for the bleed stream to be heated indirectly by a heated water stream, low pressure stream (for example 1.5 bag or less), or an alternative low temperature gentle heat source. Preferably at least a portion of the heat required is sourced from an integrated part of the plant. For example, heat can be sourced from a distillation module, or from the industrial process that provides the C1-containing substrate to the bioreactors.

Preferably the heat provided to the bleed stream is not a high-pressure heat steam. Use of high pressure or other aggressive forms of heating may cause the microorganism to denature, which results in clumping of biomass. Clumping of biomass may result in fouling within the conduits or the holding tank and compromise operation of the systems. The product stream needs to be heated for product recovery (i.e. distillation process), engineering solutions can be used to minimize the cost of heat treatment. Preferably the bleed stream is heated to a temperature sufficient to denature the enzyme responsible for the oxidation of ethanol to acetate, but lower than a temperature that would result in the clumping of the biomass.

In one embodiment, there is provided a process for depressurizing the bleed stream. In one embodiment, the dissolved, entrained or suspended $CO_2$ in the bleed stream is removed through depressurization of the bleed stream. Due to the need of $CO_2$ for the conversion of ethanol to acetate, removal of $CO_2$ from the bleed stream prevents oxidation of ethanol from occurring via this mechanism.

For this process to be effective, the bleed stream must be withdrawn from a bioreactor operated at a sufficient pressure and then depressurized such that the majority of $CO_2$ provided in the bleed stream flashes off. Preferably, substantially all the $CO_2$ in the bleed stream is flashed off. Ideally, the majority of $CO_2$ in the bleed stream should be flashed off in less than 30 seconds, or less than 20 seconds, or less than 10 seconds, or less than 5 seconds, or less than 3 seconds, or less than 2 seconds, or less than 1 second.

Ideally, the bleed stream is subjected to a pressure above atmospheric pressure for at least 1 second, or at least 3 seconds, or at least 5 seconds, or at least 10 seconds, or at least 15 seconds, or at least 20 seconds, or at least 25 seconds, or at least 30 seconds before being depressurized. Preferably, the pressure of the bleed stream is maintained at a pressure above atmospheric for between 1 to 30 seconds, or between 1 to 15 seconds, or between 15 to 30 seconds before being depressurized. In one embodiment, the bleed stream is subjected to a pressure of at least 2.0 barg, and maintained at this pressure for at least 1 second before being depressurized. In one embodiment, the pressure of the product stream is increased to at least 0.25 barg, and maintained at this pressure for at least 30 seconds before being depressurized.

In particular embodiments, where the fermentation occurs at a pressure above atmospheric, the passing of the bleed stream from a pressurized vessel to a vessel at atmospheric may provide sufficient pressure drop to provide adequate flashing of $CO_2$. In particular embodiments, the liquid exiting the bioreactor is at a pressure of least at 0.25 barg or higher and is passed to a vessel at atmospheric pressure, such pressure drop is sufficient to remove at least a portion of dissolved $CO_2$ from the liquid.

In one embodiment the microorganism contained in the bleed stream is a C1-fixing microorganism. In particular embodiments, the C1-fixing microorganism is an acetogen having a Wood-Ljungdahl pathway. In one embodiment the C1-fixing microorganism is selected from the group consisting of *Clostridium autoethanogenum, Clostridium ljungdahlii*, and *Clostridium ragsdalei.*

In one embodiment the microorganism fixes a C1-carbon source into a natively produced product. In one embodiment, the natively produced product is ethanol. In alternative embodiments, the microorganism is (i) a recombinant microorganism comprising either one or more exogenous enzymes, which produces one or more non-natively produced products; or (ii) a recombinant microorganism wherein one or more endogenous enzymes are overexpressed; or (iii) a recombinant microorganism comprising at least one genetic modification which disrupts the expression and/or activity of one or more enzymes. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), isoprene (WO 2013/180584), fatty acids (WO 2013/191567), 2-butanol (WO 2013/185123), 1,2-propanediol (WO 2014/0369152), and 1-propanol (WO 2014/0369152).

Metabolic engineering is costly and time-consuming (Keasling, Science, 330: 1355-1358, 2012). The constraints of cell membranes requiring a complete balancing of fluxes into and out of the cell makes it difficult to express biosynthetic pathways without taking into account the entire metabolic network. While there are many technologies that allow the engineer to better manipulate cells such as metabolic flux analysis, genome engineering, etc., the complexity of cells remains a limitation (Lee, Nat Chem Biol, 8: 536-546, 2012; Yadav, Metabol Eng, 14: 233-241, 2012). Furthermore, the tools we do have to regulate transcription, translation, and the genome require many design-build-test (DBT) cycles increasing the time and effort needed to optimize the biosynthesis of interest (Boyle, Metabol Eng, 14: 223-232, 2012). Although current DBT cycles are extraordinarily expensive, in vitro systems show promise in speeding up DBT cycles because they bypass many in vivo limitations by having direct access to the cellular contents (Sun, ACS Synth Biol, 3: 387-397, 2014; You, Adv Biochem Eng Biotechnol, 131: 89-119, 2013; Siegal-Gaskins, ACS Synth Biol, 3: 416-425, 2014). These in vitro systems may include, e.g., cell-free metabolic engineering using crude cell extracts (Kay, Metabol Eng, 20: 84-91, 2015) or cell-free protein synthesis for in vitro expression of enzymes (US 2006/0362708). Herein, these sorts of systems are referred to as "cell-free systems." In certain embodiments, the invention may be applied to cell-free systems to prevent the undesirable reverse reaction of a product into a precursor.

The term "non-naturally occurring" when used in reference to a microorganism is intended to mean that the microorganism has at least one genetic modification not normally found in a naturally occurring strain of the referenced species, including wild-type strains of the referenced species.

The terms "genetic modification," "genetic alteration," or "genetic engineering" broadly refer to manipulation of the genome or nucleic acids of a microorganism. Likewise, the term "genetically engineered" refers to a microorganism comprising a manipulated genome or nucleic acids. Methods of genetic modification of include, for example, heterologous gene expression, gene or promoter insertion or deletion, nucleic acid mutation, altered gene expression or inactivation, enzyme engineering, directed evolution, knowledge-based design, random mutagenesis methods, gene shuffling, and codon optimization.

"Recombinant" indicates that a nucleic acid, protein, or microorganism is the product of genetic modification, engineering, or recombination. Generally, the term "recombinant" refers to a nucleic acid, protein, or microorganism that contains or is encoded by genetic material derived from multiple sources, such as two or more different strains or species of microorganisms. As used herein, the term "recombinant" may also be used to describe a microorganism that comprises a mutated nucleic acid or protein, including a mutated form of an endogenous nucleic acid or protein.

"Wild type" refers to the typical form of an organism, strain, gene, or characteristic as it occurs in nature, as distinguished from mutant or variant forms.

"Endogenous" refers to a nucleic acid or protein that is present or expressed in the wild-type or parental microorganism from which the microorganism of the invention is derived. For example, an endogenous gene is a gene that is natively present in the wild-type or parental microorganism from which the microorganism of the invention is derived. In one embodiment, the expression of an endogenous gene may be controlled by an exogenous regulatory element, such as an exogenous promoter.

"Exogenous" refers to a nucleic acid or protein that is not present in the wild-type or parental microorganism from which the microorganism of the invention is derived. In one embodiment, an exogenous gene or enzyme may be derived from a heterologous (i.e., different) strain or species and introduced to or expressed in the microorganism of the invention. In another embodiment, an exogenous gene or enzyme may be artificially or recombinantly created and introduced to or expressed in the microorganism of the invention. Exogenous nucleic acids may be adapted to integrate into the genome of the microorganism of the invention or to remain in an extra-chromosomal state in the microorganism of the invention, for example, in a plasmid.

"Enzyme activity," or simply "activity," refers broadly to enzymatic activity, including, but not limited to, the activity of an enzyme, the amount of an enzyme, or the availability of an enzyme to catalyze a reaction. Accordingly, "increasing" enzyme activity includes increasing the activity of an enzyme, increasing the amount of an enzyme, or increasing the availability of an enzyme to catalyze a reaction. Similarly, "decreasing" enzyme activity includes decreasing the activity of an enzyme, decreasing the amount of an enzyme, or decreasing the availability of an enzyme to catalyze a reaction.

A "microorganism" is a microscopic organism, especially a bacterium, archea, virus, or fungus. The microorganism of the invention is typically a bacterium. As used herein, recitation of "microorganism" should be taken to encompass "bacterium."

The microorganism of the invention may be further classified based on functional characteristics. For example, the microorganism of the invention may be or may be derived from a C1-fixing microorganism, an anaerobe, an acetogen, an ethanologen, a carboxydotroph, and/or a methanotroph. Table 1 provides a representative list of microorganisms and identifies their functional characteristics.

TABLE 1

|  | C1-fixing | Anaerobe | Acetogen | Ethanologen | Autotroph | Carboxydotroph | Methanotroph |
| --- | --- | --- | --- | --- | --- | --- | --- |
| *Acetobacterium woodii* | + | + | + | +/−[1] | − | − | − |
| *Alkalibaculum bacchii* | + | + | + | + | + | + | − |
| *Blautia producta* | + | + | + | − | + | + | − |

TABLE 1-continued

| | C1-fixing | Anaerobe | Acetogen | Ethanologen | Autotroph | Carboxydotroph | Methanotroph |
|---|---|---|---|---|---|---|---|
| *Butyribacterium methylotrophicum* | + | + | + | + | + | + | − |
| *Clostridium aceticum* | + | + | + | − | + | + | − |
| *Clostridium autoethanogenum* | + | + | + | + | + | + | − |
| *Clostridium carboxidivorans* | + | + | + | + | + | + | − |
| *Clostridium coskatii* | + | + | + | + | + | + | − |
| *Clostridium drakei* | + | + | + | − | + | + | − |
| *Clostridium formicoaceticum* | + | + | + | − | + | + | − |
| *Clostridium ljungdahlii* | + | + | + | + | + | + | − |
| *Clostridium magnum* | + | + | + | − | + | +/−[2] | − |
| *Clostridium ragsdalei* | + | + | + | + | + | + | − |
| *Clostridium scatologenes* | + | + | + | − | + | + | − |
| *Eubacterium limosum* | + | + | + | − | + | + | − |
| *Moorella thermautotrophica* | + | + | + | + | + | + | − |
| *Moorella thermoacetica* (formerly *Clostridium thermoaceticum*) | + | + | + | −[3] | + | + | − |
| *Oxobacter pfennigii* | + | + | + | − | + | + | − |
| *Sporomusa ovata* | + | + | + | − | + | +/−[4] | − |
| *Sporomusa silvacetica* | + | + | + | − | + | +/−[5] | − |
| *Sporomusa sphaeroides* | + | + | + | − | + | +/−[6] | − |
| *Thermoanaerobacter kiuvi* | + | + | + | − | + | − | − |

[1]*Acetobacterium woodi* can produce ethanol from fructose, but not from gas.
[2]It has not been investigated whether *Clostridium magnum* can grow on CO.
[3]One strain of *Moorella thermoacetica*, *Moorella* sp. HUC22-1, has been reported to produce ethanol from gas.
[4]It has not been investigated whether *Sporomusa ovata* can grow on CO.
[5]It has not been investigated whether *Sporomusa silvacetica* can grow on CO.
[6]It has not been investigated whether *Sporomusa sphaeroides* can grow on CO.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium. In a preferred embodiment, the microorganism of the invention is derived from a C1-fixing microorganism identified in Table 1.

An "anaerobe" is a microorganism that does not require oxygen for growth. An anaerobe may react negatively or even die if oxygen is present above a certain threshold. Typically, the microorganism of the invention is an anaerobe. In a preferred embodiment, the microorganism of the invention is derived from an anaerobe identified in Table 1.

An "acetogen" is a microorganism that produces or is capable of producing acetate (or acetic acid) as a product of anaerobic respiration. Typically, acetogens are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). Acetogens use the acetyl-CoA pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen. In a preferred embodiment, the microorganism of the invention is derived from an acetogen identified in Table 1.

An "ethanologen" is a microorganism that produces or is capable of producing ethanol. Typically, the microorganism of the invention is an ethanologen. In a preferred embodiment, the microorganism of the invention is derived from an ethanologen identified in Table 1.

An "autotroph" is a microorganism capable of growing in the absence of organic carbon. Instead, autotrophs use inorganic carbon sources, such as CO and/or $CO_2$. Typically, the microorganism of the invention is an autotroph. In a preferred embodiment, the microorganism of the invention is derived from an autotroph identified in Table 1.

A "carboxydotroph" is a microorganism capable of utilizing CO as a sole source of carbon. Typically, the microorganism of the invention is a carboxydotroph. In a preferred embodiment, the microorganism of the invention is derived from a carboxydotroph identified in Table 1.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

More broadly, the microorganism of the invention may be derived from any genus or species identified in Table 1.

In a preferred embodiment, the microorganism of the invention is derived from the cluster of Clostridia comprising the species *Clostridium autoethanogenum*, *Clostridium ljungdahlii*, and *Clostridium ragsdalei*. These species were first reported and characterized by Abrini, *Arch Microbiol*, 161: 345-351, 1994 (*Clostridium autoethanogenum*), Tanner, *Int J System Bacteriol*, 43: 232-236, 1993 (*Clostridium ljungdahlii*), and Huhnke, WO 2008/028055 (*Clostridium ragsdalei*).

These three species have many similarities. In particular, these species are all C1-fixing, anaerobic, acetogenic, ethanologenic, and carboxydotrophic members of the genus *Clostridium*. These species have similar genotypes and phenotypes and modes of energy conservation and fermentative metabolism. Moreover, these species are clustered in clostridial rRNA homology group I with 16S rRNA DNA that is more than 99% identical, have a DNA G+C content of about 22-30 mol %, are gram-positive, have similar morphology and size (logarithmic growing cells between 0.5-0.7×3-5 μm), are mesophilic (grow optimally at 30-37° C.), have similar pH ranges of about 4-7.5 (with an optimal pH of about 5.5-6), lack cytochromes, and conserve energy via an Rnf complex. Also, reduction of carboxylic acids into their corresponding alcohols has been shown in these species (Perez, *Biotechnol Bioeng*, 110:1066-1077, 2012). Importantly, these species also all show strong autotrophic growth on CO-containing gases, produce ethanol and acetate (or acetic acid) as main fermentation products, and produce small amounts of 2,3-butanediol and lactic acid under certain conditions.

However, these three species also have a number of differences. These species were isolated from different sources: *Clostridium autoethanogenum* from rabbit gut, *Clostridium ljungdahlii* from chicken yard waste, and *Clostridium ragsdalei* from freshwater sediment. These species differ in utilization of various sugars (e.g., rhamnose, arabinose), acids (e.g., gluconate, citrate), amino acids (e.g., arginine, histidine), and other substrates (e.g., betaine, butanol). Moreover, these species differ in auxotrophy to certain vitamins (e.g., thiamine, biotin). These species have differences in nucleic and amino acid sequences of Wood-Ljungdahl pathway genes and proteins, although the general organization and number of these genes and proteins has been found to be the same in all species (Köpke, *Curr Opin Biotechnol*, 22: 320-325, 2011).

Thus, in summary, many of the characteristics of *Clostridium autoethanogenum*, *Clostridium ljungdahlii*, or *Clostridium ragsdalei* are not specific to that species, but are rather general characteristics for this cluster of C1-fixing, anaerobic, acetogenic, ethanologenic, and carboxydotrophic members of the genus *Clostridium*. However, since these species are, in fact, distinct, the genetic modification or manipulation of one of these species may not have an identical effect in another of these species. For instance, differences in growth, performance, or product production may be observed.

The microorganism of the invention may also be derived from an isolate or mutant of *Clostridium autoethanogenum*, *Clostridium ljungdahlii*, or *Clostridium ragsdalei*. Isolates and mutants of *Clostridium autoethanogenum* include JA1-1 (DSM10061) (Abrini, *Arch Microbiol*, 161: 345-351, 1994), LBS1560 (DSM19630) (WO 2009/064200), and LZ1561 (DSM23693). Isolates and mutants of *Clostridium ljungdahlii* include ATCC 49587 (Tanner, *Int J Syst Bacteriol*, 43: 232-236, 1993), PETCT (DSM13528, ATCC 55383), ERI-2 (ATCC 55380) (U.S. Pat. No. 5,593,886), C-01 (ATCC 55988) (U.S. Pat. No. 6,368,819), O-52 (ATCC 55989) (U.S. Pat. No. 6,368,819), and OTA-1 (Tirado-Acevedo, Production of bioethanol from synthesis gas using *Clostridium ljungdahlii*, PhD thesis, North Carolina State University, 2010). Isolates and mutants of *Clostridium ragsdalei* include PI 1 (ATCC BAA-622, ATCC PTA-7826) (WO 2008/028055).

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The substrate generally comprises at least some amount of CO, such as about 1, 2, 5, 10, 20, 30, 40, 50, 60, 70, 80, 90, or 100 mol % CO. The substrate may comprise a range of CO, such as about 20-80, 30-70, or 40-60 mol % CO. Preferably, the substrate comprises about 40-70 mol % CO (e.g., steel mill or blast furnace gas), about 20-30 mol % CO (e.g., basic oxygen furnace gas), or about 15-45 mol % CO (e.g., syngas). In some embodiments, the substrate may comprise a relatively low amount of CO, such as about 1-10 or 1-20 mol % CO. The microorganism of the invention typically converts at least a portion of the CO in the substrate to a product. In some embodiments, the substrate comprises no or substantially no (<1 mol %) CO.

The substrate may comprise some amount of $H_2$. For example, the substrate may comprise about 1, 2, 5, 10, 15, 20, or 30 mol % $H_2$. In some embodiments, the substrate may comprise a relatively high amount of $H_2$, such as about 60, 70, 80, or 90 mol % $H_2$. In further embodiments, the substrate comprises no or substantially no (<1 mol %) $H_2$.

The substrate may comprise some amount of $CO_2$. For example, the substrate may comprise about 1-80 or 1-30 mol % $CO_2$. In some embodiments, the substrate may comprise less than about 20, 15, 10, or 5 mol % $CO_2$. In another embodiment, the substrate comprises no or substantially no (<1 mol %) $CO_2$.

Although the substrate is typically gaseous, the substrate may also be provided in alternative forms. For example, the substrate may be dissolved in a liquid saturated with a CO-containing gas using a microbubble dispersion generator. By way of further example, the substrate may be adsorbed onto a solid support.

The substrate and/or C1-carbon source may be a waste gas obtained as a by-product of an industrial process or from some other source, such as from automobile exhaust fumes or biomass gasification. In certain embodiments, the industrial process is selected from the group consisting of ferrous metal products manufacturing, such as a steel mill manufacturing, non-ferrous products manufacturing, petroleum refining, coal gasification, electric power production, carbon black production, ammonia production, methanol production, and coke manufacturing. In these embodiments, the substrate and/or C1-carbon source may be captured from the industrial process before it is emitted into the atmosphere, using any convenient method.

The substrate and/or C1-carbon source may be syngas, such as syngas obtained by gasification of coal or refinery residues, gasification of biomass or lignocellulosic material, or reforming of natural gas. In another embodiment, the syngas may be obtained from the gasification of municipal solid waste or industrial solid waste.

The composition of the substrate may have a significant impact on the efficiency and/or cost of the reaction. For example, the presence of oxygen (O2) may reduce the efficiency of an anaerobic fermentation process. Depending on the composition of the substrate, it may be desirable to treat, scrub, or filter the substrate to remove any undesired impurities, such as toxins, undesired components, or dust particles, and/or increase the concentration of desirable components.

In certain embodiments, the fermentation is performed in the absence of carbohydrate substrates, such as sugar, starch, lignin, cellulose, or hemicellulose.

In addition to one or more target products, the microorganism of the invention may also produce one or more co-product. For instance, in addition to the target product, the invention may produce acetate, 2,3-butanediol, butanol, butyrate, lactate, butene, butadiene, methyl ethyl ketone, ethylene, acetone, isopropanol, lipids, 3-hydroxypropionate, isoprene, fatty acids, 2-butanol, 1,2-propanediol, and/or 1-propanol. In certain embodiments, microbial biomass itself may be considered a product or co-product.

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

"Increasing the efficiency," "increased efficiency," and the like include, but are not limited to, increasing growth rate, product production rate or volume, product volume per volume of substrate consumed, or product selectivity. Efficiency may be measured relative to the performance of a parental microorganism from which the microorganism of the invention is derived.

FIG. 1 depicts a representative bioreactor system comprising a first bioreactor 10 and a second bioreactor 20. The bioreactor system receives a C1-containing substrate 12. The C1-containing substrate is divided into a first bioreactor gas inlet stream 14 and a second bioreactor gas inlet stream 14', which are fed, respectively, to first and second bioreactors 10, 20 through their respective gas inlets 16, 16'.

The bacteria concentration in-liquid phase zones 18, 18' of bioreactors 10, 20 can be maintained at varying levels of ethanol productivity by providing a means whereby filtered and unfiltered parts of liquid may be withdrawn. Liquid is withdrawn from the first bioreactor 10 via a permeate stream 28, which is filtered by a filtration system 25 to remove bacteria, and a bleed stream 26, which is unfiltered and contains C1-fixing bacteria (biomass) in substantially the same concentration as in the fermentation broth in continuous liquid phase zone 18 of first bioreactor 10. Filtered bacteria is returned to the first bioreactors 10 via conduit 36. Liquid products withdrawn from first bioreactor 10 may therefore comprise both permeate stream 28 and bleed stream 26. In the same manner, a second filtration system 25' is provided in communication with continuous liquid phase zone 18', and allows for the withdrawal of bleed stream 40 and permeate stream 50 from a final bioreactor of bioreactor system, with the return of filtered bacteria 36' to continuous liquid phase zone 18' of second bioreactor 20.

Liquid culture medium may be fed, through culture medium inlet 34 to bioreactor system, and in particular to first bioreactor 10, to supply nutrients for maintaining bacterial growth and to replace the liquid volume lost in intermediate liquid product 32 withdrawn from first bioreactor 10, all or a portion of which may be passed to second bioreactor 20. Optionally, liquid culture medium may be fed to second bioreactor 20 via medium inlet 34'. Optionally, portions of bleed stream 26 and/or permeate stream 28 may be withdrawn from bioreactor system (e.g., for process monitoring and analysis), without passing to second bioreactor 20.

Gas outlet streams 38, 38' may be withdrawn from conduits in fluid communication with a bioreactor headspace 22, 22'. Gas outlet streams 38, 38' may be withdrawn separately from bioreactor system or, combined and then withdrawn as gaseous product outlet 24.

Accordingly, FIG. 1 depicts a bioreactor system in which gaseous C1-containing substrate 12 can be fed in parallel to first and second bioreactors 10, 20, whereas liquid products, which can include C1-fixing bacteria (biomass), can be fed successively from first bioreactor 10 to second bioreactor 20. In the embodiment of FIG. 1, the final bioreactor, from which bleed stream 40 and permeate stream 50 are withdrawn from bioreactor system 100, is namely second bioreactor 20. In alternative embodiments having bioreactor systems with additional bioreactors (e.g., three or four bioreactors), and specifically one or more intermediate bioreactors downstream of a first bioreactor and upstream of a final bioreactor, the gaseous and liquid feeds may be introduced to such intermediate bioreactors in a similar manner, and the gaseous and liquid products may be withdrawn from such intermediate bioreactors in a similar manner. Liquid product streams, including bleed and permeate streams, may be passed to and from successive bioreactors in a similar manner.

In general, one or more metabolite products (e.g., ethanol) of bioreactor system 100 is recovered from bleed and permeate streams, or portions thereof, withdrawn from a final bioreactor, such as bleed stream 40 and permeate stream 50 withdrawn from second bioreactor 20 in the embodiment of FIG. 1. Optionally, such metabolite products may also be recovered from bleed and/or permeate streams, or portions thereof, withdrawn from one or more bioreactors other than a final bioreactor.

Figure 2:
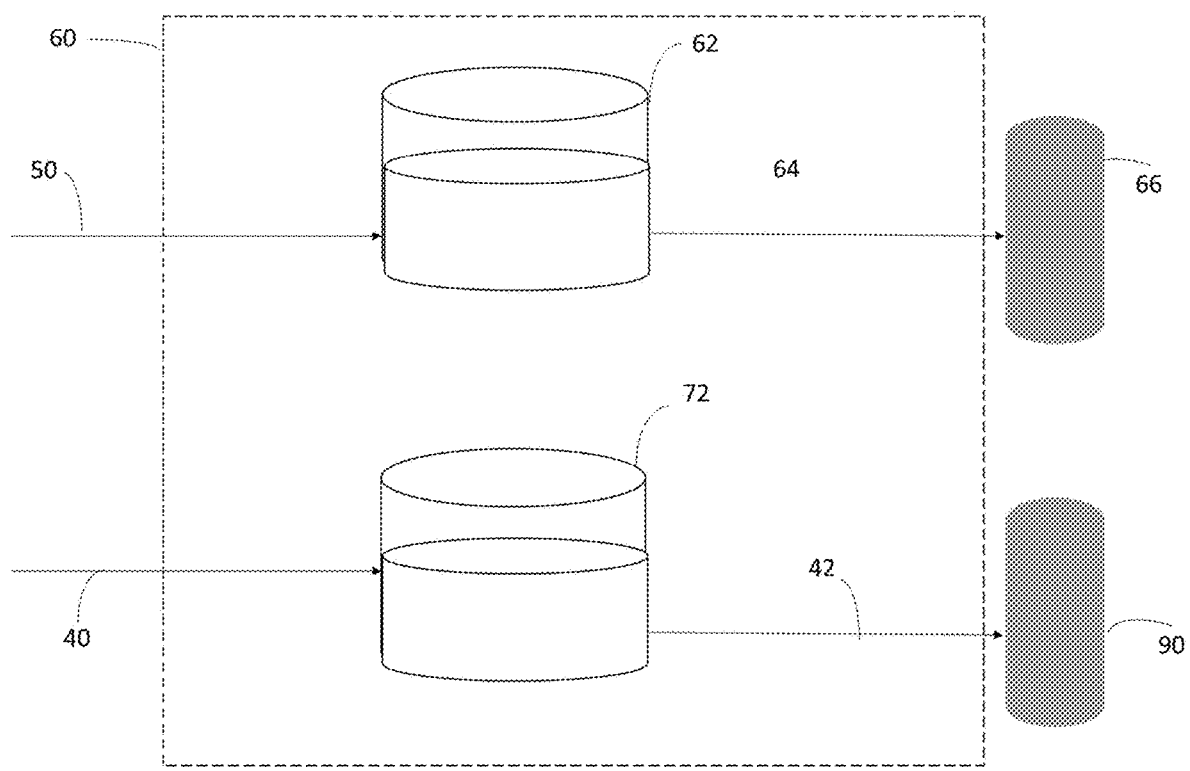
FIG. 2 depicts a representative system including a storage zone which receives permeate and bleed streams from a bioreactor system of FIG. 1, and provides streams to product recovery module.

As shown in FIG. 2, permeate stream 50 and bleed stream 40 from bioreactor are fed to a storage zone. Permeate stream is fed to permeate holding tank 62. Permeate may undergo one or more treatment steps, such as a clarification step, prior to being passed to a permeate product recovery module 66, via conduit 64. Bleed stream is fed to a bleed holding tank 72, wherein bleed stream undergoes one or more treatment steps to prevent conversion of ethanol to acetate in the bleed stream. The treatment step may comprise heating of the bleed stream, depressurizing of the bleed stream, or displacement of $CO_2$ from the bleed stream. Heating of treated stream may be carried out either in the holding tank, or in a conduit provided between the bioreactor and the holding tank. Preferentially energy for heating the bleed stream is sourced from an industrial process located adjacent to the bioreactor system. The treated stream 42 is then fed to a bleed product recovery module 90, and ethanol is recovered from the treated stream. Optionally permeate stream 50 and bleed stream 40 are combined, and storage zone receives a combined stream fed to a single holding tank. (not shown).

Figure 3A:
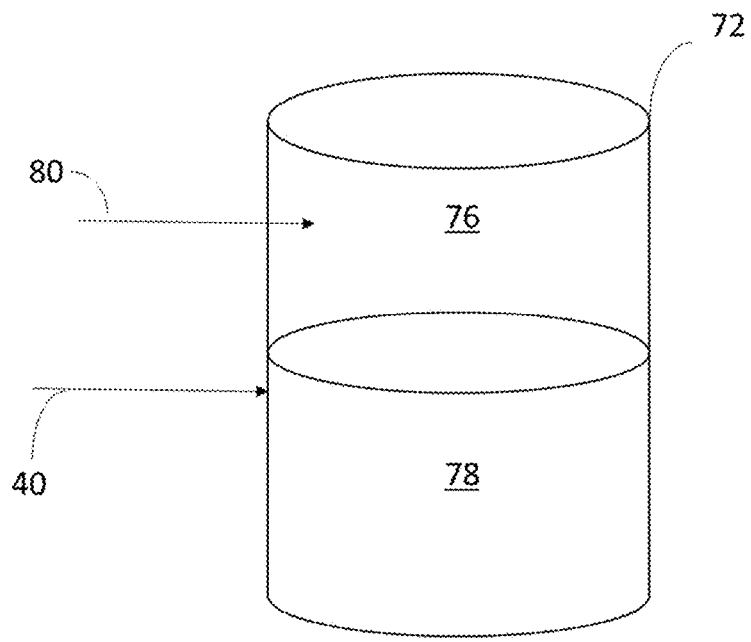
FIG. 3a, FIG. 3b, FIG. 3c and FIG. 3d depict various arrangements of the holding tank according to various embodiments for displacing $CO_2$ from the bleed stream

FIG. 3a depicts a bleed holding tank 72 according to one aspect of the invention. Bleed stream 40 is fed to a bleed holding tank 72. In one embodiment inert gas 80, such as nitrogen, may be continuously sparged into a headspace 76 of the bleed holding tank 72, while a portion of the headspace is continuously exhausted via a vent (not shown).

Figure 3B:
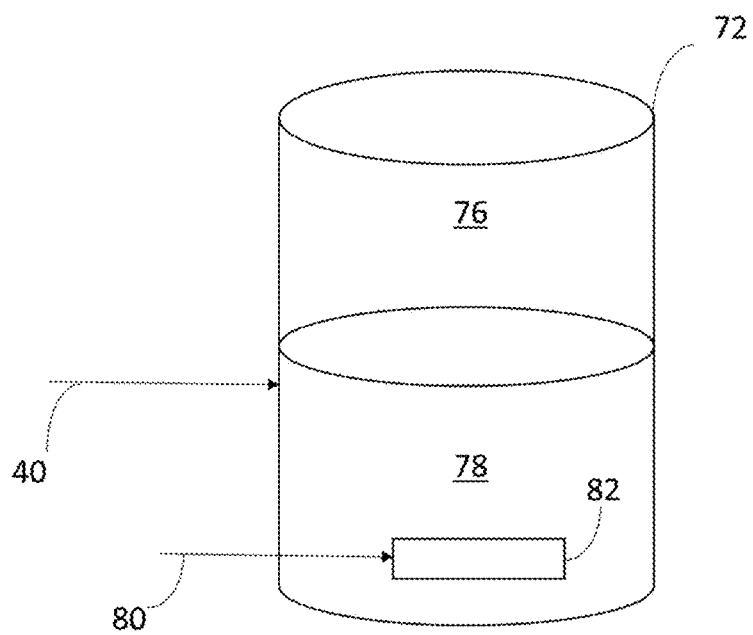

FIG. 3b shows an alternative system wherein nitrogen 80 is fed to the bleed stream via an inlet 82 provided in a liquid portion 78 of the bleed holding tank 78.

Figure 3C:
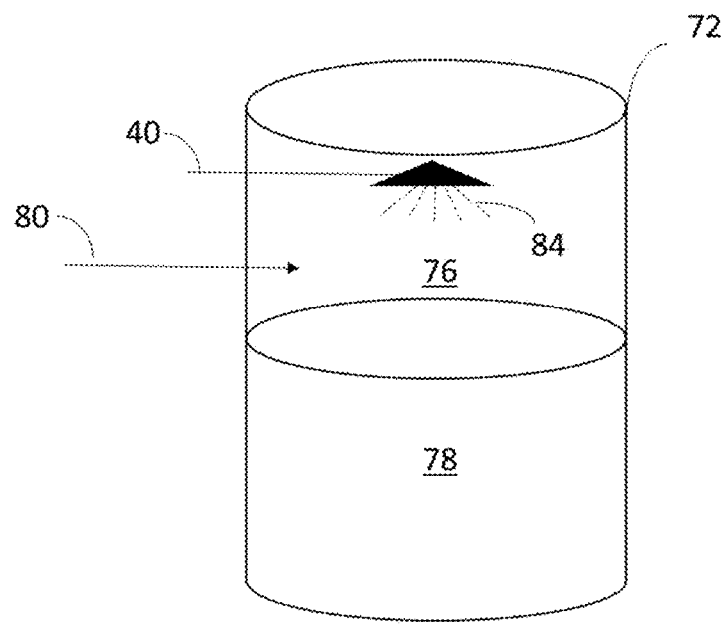

FIG. 3c shows an embodiment, wherein the bleed stream 40 is sprayed into a nitrogen containing headspace 76 of the bleed holding tank 72 via one or more nozzles 84.

Figure 3D:
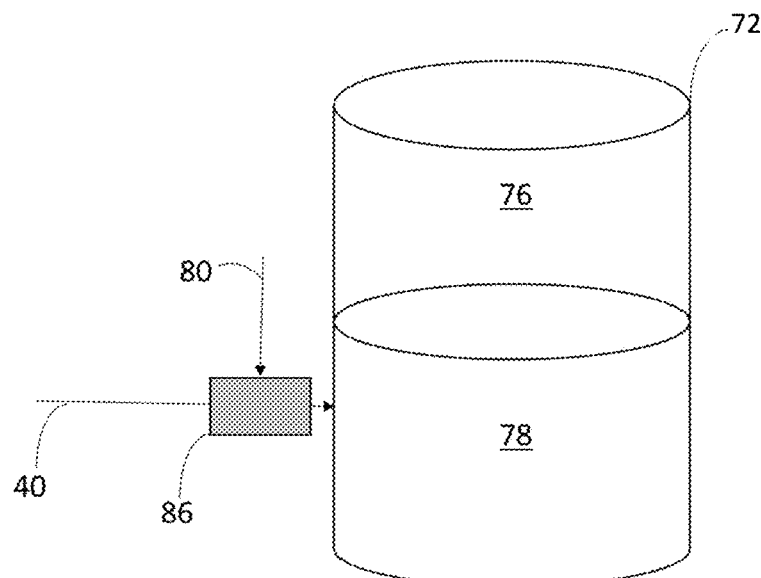

FIG. 3d shows an embodiment, wherein nitrogen 80 is sparged into the bleed stream in an inline sparger 86 provided upstream of the holding tank 72.

EXAMPLES

The following examples further illustrate the invention but, of course, should not be construed to limit its scope in any way.

*C. autoethanogenum* DSM23693 (a derivate of DSM10061) was obtained from DSMZ (The German Collection of Microorganisms and Cell Cultures, Inhoffenstraße 7B, 38124 Braunschweig, Germany). Growth was carried out at 37° C. using strictly anaerobic conditions and techniques (Hungate, Meth Microbiol, 3B: 117-132, 1969; Wolfe, Adv Microb Physiol, 6: 107-146, 1971). Chemically defined PETC medium without yeast extract was used. A 30 psi CO-containing gas mix (44% CO, 32% $N_2$, 22% $CO_2$, 2% $H_2$) served as a sole source of carbon and energy.

| PETC medium | Per 1.0 L of medium |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Resazurin (2 g/L stock) | 0.5 ml |
| $NaHCO_3$ | 2 g |
| Reducing agent solution | 0.006-0.008% (v/v) |
| Distilled water | Up to 1.0 L |
| | pH 5.5 (adjusted with HCl) |

| Wolfe's vitamin solution | Per 1.0 L of solution |
|---|---|
| Biotin | 2 mg |
| Folic acid | 2 mg |
| Pyridoxine hydrochloride | 10 mg |
| Riboflavin | 5 mg |
| Nicotinic acid | 5 mg |
| Calcium D-(+)-pantothenate | 5 mg |
| Vitamin B12 | 0.1 mg |
| p-Aminobenzoic acid | 5 mg |
| Lipoic acid | 5 mg |
| Thiamine | 5 mg |
| Distilled water | To 1.0 L |

| Trace metal solution | Per 1.0 L of solution |
|---|---|
| Nitrilotriacetic acid | 2 g |
| $MnSO_4 \cdot H_2O$ | 1 g |
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1.0 L |

| Reducing agent solution | Per 100 mL of solution |
|---|---|
| NaOH | 0.9 g |
| Cysteine•HCl | 4 g |
| $Na_2S$ | 4 g |
| Distilled water | To 100 mL |

Example 1: $CO_2$ Displacement to Prevent Ethanol Oxidation

Fermentation with *C. autoethanogenum* DSM23693 were carried out in 1.5 L bioreactors at 37° C. To achieve anaerobicity the reactor vessel was sparged with nitrogen. Prior to inoculation, the gas was switched to pure gases fed continuously to the reactor. (42% CO, 1.5% $CO_2$, 11% $N_2$, 42% Hz), pH was adjusted to 5.0 using ammonium hydroxide (5M). The gas flow was initially set at 59 ml/min/L, increasing to 118 ml/min/L during mid-exponential phase, while the agitation was increased from 200 rpm to 800 rpm. Na2S (0.5M) was dosed into the bioreactor at 0.2 ml/hr. Once the OD600 reached 1.1, the bioreactor was switched to a continuous mode at a dilution rate of 1.95 d−1 and a bacterial dilution rate of 1.0 d−1. During continuous mode gas and agitation were adjusted to 267 ml/min/L and 950 rpm, respectively with the bacterial dilution rate adjusted down to 0.35 d−1. $Na_2S$ was increased to 0.5 ml/hr. Media samples were taken to measure the biomass and metabolites and a headspace analysis of the in- and outflowing gas was performed on regular basis. By day 16.0 fermentation metabolites and biomass were stable with the concentration of ethanol and acetate at 26.5 g/L and 4.75 g/L, CO uptake at 5.9 mol/L/d and Hz uptake at 3.45 mol/L/d.

On day 16.95 broth samples (25 mL) of the fermentation were taken, in triplicate, and placed in a simulated holding tank (anaerobic serum bottle), the headspace of the serum bottle was exchanged and pressurized with either $CO_2$ or $N_2$. Care was taken to ensure no $O_2$ introduction occurred during this process. Metabolite samples were then taken over a period of 3 h and measured on an HPLC.

Figure 4:
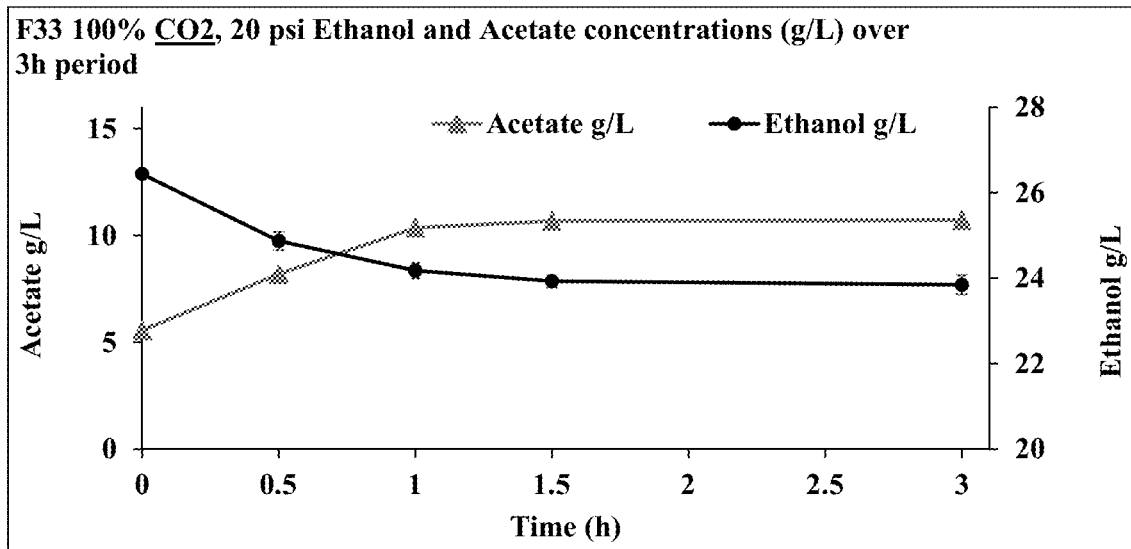
FIG. 4: Metabolite concentrations over time when cells, in triplicate, are taken from a bioreactor and placed in a $CO_2$ headspace
Figure 5:
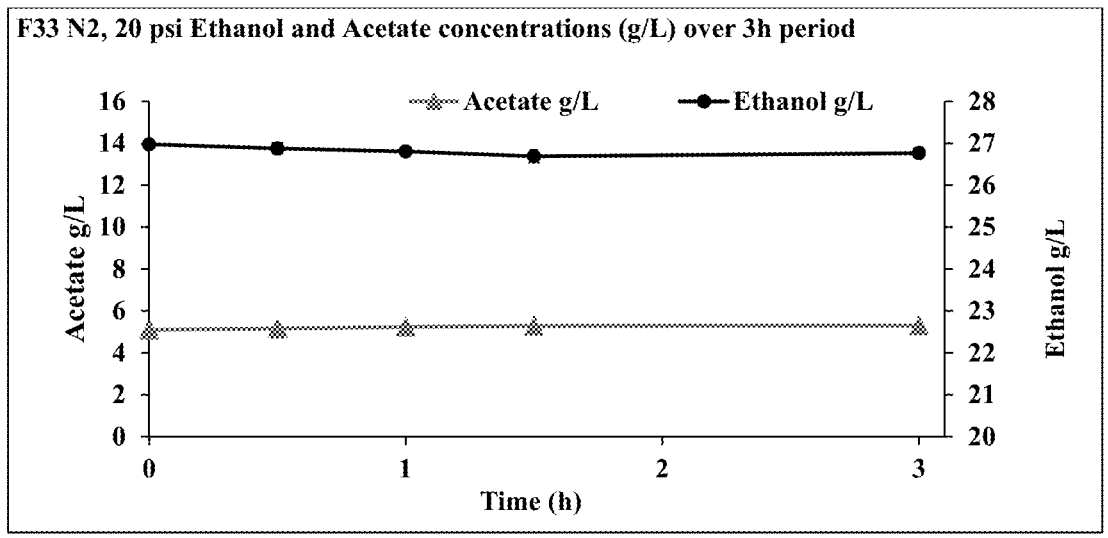
FIG. 5: Metabolite concentrations over time when cells, in triplicate, are taken from a bioreactor and placed in an $N_2$ headspace.

FIGS. 4 and 5 show the change in Ethanol and Acetate under the two conditions. In the example where $CO_2$ headspace was used (FIG. 4) Acetate increases from 5.5 g/L to 10.67 g/L and ethanol decreases from 26.4 g/l to 23.8 g/L. This demonstrates significant ethanol oxidation.

FIG. 5 shows that when the same cells are placed in an $N_2$ headspace there is no significant change in metabolite concentration and no ethanol oxidation. Metabolite concentrations remain the same as measured in the fermentation.

Example 2: Heat Treatment to Prevent Ethanol Oxidation

A single sample was collected from a CSTR experiment, which was operated under similar conditions to the experiments described in Example 1, and was divided into sub-samples. The sub-samples were stored under conditions representative of the conditions for the biomass containing product streams post fermentation, prior to product recovery. Under these conditions, conversion of ethanol to acetate was expected.

The sub-samples were independently heat treated at varying time intervals, from 0-240 minutes. Heat treatment involved holding samples at 80° C. for 5 minutes.

Acetate and ethanol titres were measured by HPLC after heat treatment, and compared to the corresponding time zero heat treated sample.

Figure 6:
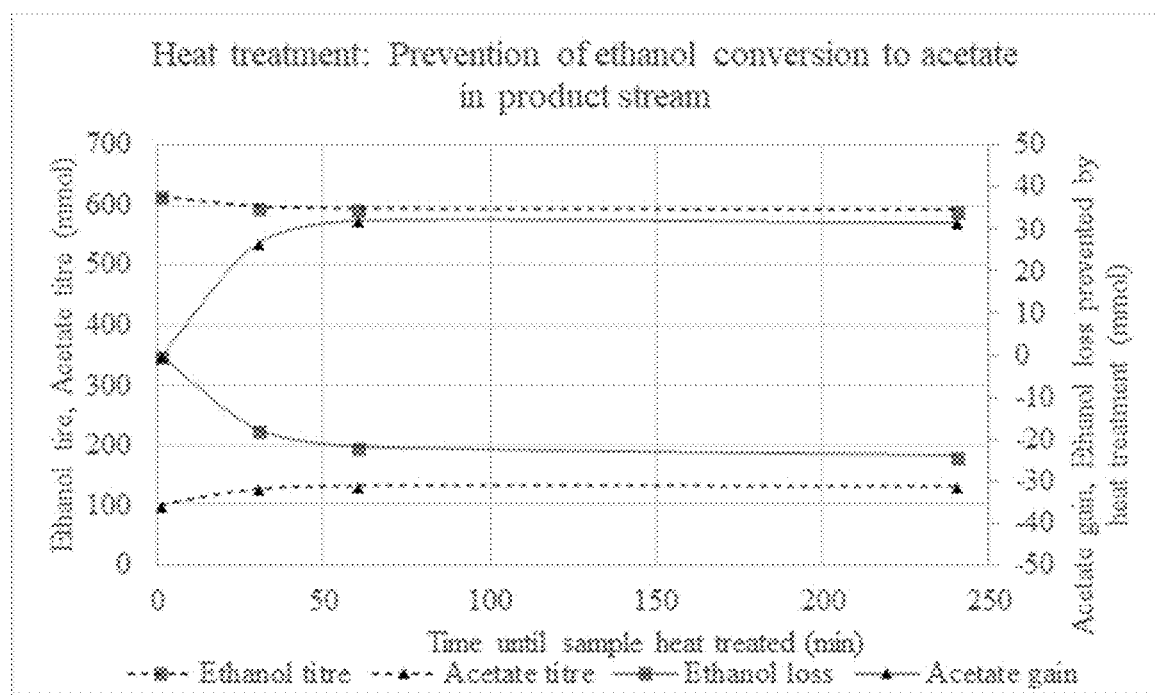
FIG. 6 shows change in acetate and ethanol titres over time, correlating acetate gain/ethanol loss, and effect of heat treatment on ethanol loss.

FIG. 6 shows the comparison between the sub-samples, heat treated at different time points. The solid-line on the graph shows the respective loss of ethanol over time if a sub-sample was not heat treated immediately. The difference between any two data points indicates the amount of conversion occurring in that time period. The difference between the time zero and time 240 estimates the absolute benefit of heat treatment. As shown, between 60 minutes and 240 minutes there is little further conversion, thus beyond 240 minutes little further conversion would likely occur.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for reducing bio-catalytic oxidation of alcohol, the process comprising:
    a. withdrawing a bleed stream from a bioreactor, the bleed stream comprising $CO_2$, an alcohol, and at least one enzyme capable of oxidizing the alcohol, and
    b. treating the bleed stream to reduce oxidation of the alcohol by the enzyme, wherein treating comprises at least one of
        (i) sparging the bleed stream with a nitrogen gas;
        (ii) increasing the temperature of the bleed stream; and
        (iii) depressurizing the bleed stream.

2. The process of claim 1, wherein the alcohol is ethanol.

3. The process of claim 1, wherein the at least one enzyme capable of oxidizing alcohol is selected from the group consisting of NADH dependent alcohol dehydrogenase (EC1.1.1.1), NADPH dependent alcohol dehydrogenase (EC1.1.1.2), aldehyde: ferredoxin oxiodreductase (EC1.2.7.5), acetate kinase (EC2.1.2.1), and phosphotransacetylase (EC 2.3.1.8).

4. The process of claim 1, wherein the enzyme is produced by a C1-fixing bacterium.

5. The process of claim 1, wherein the enzyme is produced by a non-C1-fixing bacterium.

6. The process of claim 1, wherein the enzyme is present in a C1-fixing bacterium.

7. The process of claim 1, wherein the enzyme is present in a non-C1-fixing bacterium.

8. The process of claim 4, wherein the C1-fixing bacterium is present in the bleed stream.

9. The process of claim 5, wherein the non-C1-fixing bacterium is present in the bleed stream.

10. The process of claim 1, wherein the temperature of the bleed stream is increased to a temperature at which the enzyme is denatured.

11. The process of claim 10, wherein the temperature of the bleed stream is increased to at least 60° C.

12. The process of claim 10, wherein the bleed stream is maintained a temperature of at least 60° C. for at least 5 seconds.

13. The process of claim 1, wherein the treatment step comprises sparging the bleed stream with nitrogen gas, and, wherein the nitrogen gas displaces at least a portion of the $CO_2$ from the bleed stream.

14. The process of claim 13, wherein the nitrogen gas displaces substantially all of the $CO_2$ from the bleed stream.

15. The process of claim 1, wherein the treatment step comprises depressurizing the bleed stream, wherein at least a portion of the $CO_2$ from the bleed stream is flashed off.

16. A process for reducing bio-catalytic oxidation of ethanol in a product stream, wherein the product stream comprises a primary alcohol, dissolved $CO_2$, and at least one enzyme capable of oxidizing the alcohol, the process comprising:
    a. withdrawing a product stream from a reactor; and
    b. treating the product stream to reduce the oxidation of the alcohol.

17. The process of claim 16, wherein the alcohol is selected from the group consisting of ethanol, butanol, 1-propanol and 1-octanol.

18. The process of claim 4, wherein the C1-fixing bacterium is selected from *Clostridium autoethanogenum*, *Clostridium ljungdahlii*, and *Clostridium ragsdalei*.

19. The process of claim 6, wherein the C1-fixing bacterium is selected from *Clostridium autoethanogenum*, *Clostridium ljungdahlii*, and *Clostridium ragsdalei*.

* * * * *